(12) United States Patent
Kai et al.

(10) Patent No.: US 7,417,118 B2
(45) Date of Patent: Aug. 26, 2008

(54) PHARMACEUTICAL COMPOSITION CONTAINING ARTIFICIAL OXYGEN CARRIER

(75) Inventors: Toshiya Kai, Osaka (JP); Naohisa Katayama, Osaka (JP); Yuko Azuma, Osaka (JP); Junichi Yokoe, Osaka (JP); Yoshinori Kida, Osaka (JP); Ippei Hukutomi, Osaka (JP); Makoto Sato, Osaka (JP); Eishun Tsuchida, Tokyo-to (JP); Shinji Takeoka, Tokyo-to (JP); Teruyuki Komatsu, Tachikawa (JP); Hiromi Sakai, Tokyo-to (JP); Keitaro So, Tokyo-to (JP)

(73) Assignee: Nipro Corporation, Osaka (JP)

( * ) Notice: Subject to any disclaimer, the term of this patent is extended or adjusted under 35 U.S.C. 154(b) by 26 days.

(21) Appl. No.: 10/819,352

(22) Filed: Apr. 7, 2004

(65) Prior Publication Data
US 2004/0258745 A1      Dec. 23, 2004

(30) Foreign Application Priority Data
Apr. 8, 2003    (JP) ............................. 2003-103875

(51) Int. Cl.
*C07K 1/00*    (2006.01)
(52) U.S. Cl. .................................................... 530/350
(58) Field of Classification Search ................ 424/450, 424/600; 514/6
See application file for complete search history.

(56) References Cited

U.S. PATENT DOCUMENTS

| | | | |
|---|---|---|---|
| 4,133,874 A | 1/1979 | Miller et al. | |
| 4,412,989 A | 11/1983 | Iwashita et al. | |
| 4,425,334 A | 1/1984 | Hunt | |
| 5,589,189 A * | 12/1996 | Moynihan | 424/450 |
| 2002/0120096 A1 | 8/2002 | Tsuchida et al. | |

FOREIGN PATENT DOCUMENTS

| EP | 0 099 652 A2 | 2/1984 |
|---|---|---|
| EP | 0 170 247 A2 | 2/1986 |
| EP | 0 354 855 A2 | 2/1990 |
| JP | 55-72110 A | 5/1980 |
| JP | 58-213779 A | 12/1983 |
| JP | 2-6337 B2 | 2/1990 |
| JP | 3-218309 A | 9/1991 |
| JP | 4-5242 A | 1/1992 |
| WO | 98/08500 A1 | 3/1998 |

OTHER PUBLICATIONS

Vandegriff et al., Encapsulation of hemoglobin in non-phospholipid vesicles.☐☐Artif Cells Blood Substit Immobil Biotechnol. 1994;22(3):849-54.*
Phillips et al., Polyethylene glycol-modified liposome-encapsulated hemoglobin: a long circulating red cell substitute. J Pharmacol Exp Ther. Feb. 1999;288(2):665-70.*
Silvius, John R. et al., "Interbilayer Transfer of Phospholipid-Anchored Macromolecules via Monomer Diffusion," *Biochemistry*, vol. 32, 1993, pp. 3153-3161.
Sakai, Hiromi, et al., "Synthesis and Physicochemical Characterization of a Series of Hemoglobin-Based Oxygen Carriers: Objective Comparison between Cellular and Acellular Types", *Bioconjugate Chem.*, vol. 11, No. 1, pp. 56-64 (2000).
Sakai, Hiromi, et al., "Characteristics of Bovine Hemoglobin as a Potential Source of Hemoglobin-Vesicles for an Artificial Oxygen Carrier", *J. Biochem*, vol. 131, No. 4, pp. 611-617 (2002).

* cited by examiner

*Primary Examiner*—Robert B. Mondesi
(74) *Attorney, Agent, or Firm*—Kubovcik & Kubovcik (57) ABSTRACT

A pharmaceutical composition containing an artificial oxygen carrier, which has high oxygen carrying efficiency; and has a required colloid osmotic pressure, an appropriate crystalloid osmotic pressure, pH, and electrolyte balance. The composition is prepared by appropriately adding at least one substance selected from the group consisting of a compound capable of providing a colloid osmotic pressure, an electrolyte, a saccharide, an amino acid, an antioxidant, a pH adjuster, and an isotonizing agent to a preparation including a liposome-encapsulated hemoglobin in which a hemoglobin is encapsulated in a liposome or to a preparation including a conjugate of a porphyrin-iron complex and albumin.

5 Claims, 5 Drawing Sheets

PHARMACEUTICAL COMPOSITION CONTAINING ARTIFICIAL OXYGEN CARRIER

TECHNICAL FIELD OF THE INVENTION

The present invention relates to a pharmaceutical composition containing an artificial oxygen carrier capable of adsorbing and desorbing oxygen reversibly in a living body.

More specifically, the present invention relates to a pharmaceutical composition that is used in medical fields for supplying oxygen to an ischemic site or a tumor tissue or for blood infusion to a massive bleeding patient, or used as an organ storage perfusion solution, as an extracorporeal circulation solution, or as a cell culture solution; has high oxygen carrying efficiency; has a required colloid osmotic pressure, an appropriate crystalloid osmotic pressure, pH, and electrolyte balance; and contains a metal complex having a porphyrin structure.

BACKGROUND OF THE INVENTION

It is known that a plasma protein, which is a plasma colloid, plays an important role in maintaining the amount of blood in blood vessels of a living body. Therefore, up to now, techniques for fluid replacement with a plasma expander having a colloid osmotic pressure approximately equal to that of blood of a living body have been applied for recovering hemorrhagic shock of a patient. However, in the case where a patient bleeds in an amount of 30% or more of the circulating blood, oxygen is insufficiently provided to peripheral tissues, so that the patient requires administration of an oxygen carrier in addition to a plasma expander.

Conventionally, natural blood containing natural erythrocytes or an erythrocyte concentrated solution has been used as such an oxygen carrier. However, in order to avoid blood clot caused by antigen-antibody reaction, it is required that the blood type of a donor matches that of a receptor and cross-compatibility is performed when in use. In addition, the effective storage period of such natural blood or erythrocyte concentrated solution is as short as 3 weeks (4° C.). Frozen blood capable of long-term storage has problems such as high cost and occurrence of hemolysis by osmotic pressure shock when using it. Moreover, occurrence of infectious diseases such as hepatitis and acquired immunodeficiency syndrome was also a concern.

In order to solve the aforementioned problems, the following studies have already been disclosed: a study on an artificial oxygen carrier composed of a fluorocarbon emulsion (JP 60-33367); a study on a blood substitute for extending retention time of hemoglobin (such as human hemoglobin, bovine hemoglobin, and recombinant hemoglobin, hereinafter abbreviated to Hb), which is a heme protein having functions of adsorbing and desorbing oxygen reversibly and of dissociation, in circulating blood by binding polyethylene glycol (hereinafter abbreviated to PEG) or the like to hemoglobin for modification (JP 2-6337); or the like.

However, the oxygen carrying ability of the artificial oxygen carrier composed of a fluorocarbon emulsion depends on a physical oxygen dissolving phenomenon in fluorocarbon. Therefore, the oxygen carrying ability is insufficient. A blood substituent in which Hb binds to PEG or the like also has a problem of insufficient hemoglobin retention time.

The development of an oxygen infusion using Hb such as intramolecular crosslinking Hb, water-soluble polymer bound Hb, or intermolecular crosslinking polymerization Hb has been advanced. However, the oxygen infusion has been found to have various side effects caused by the non-cell structure.

Reasons that Hb is naturally encapsulated in erythrocyte membrane are shown in the following items:

1) to enable controlling a colloid osmotic pressure by being encapsulated by erythrocyte membrane because the colloid osmotic pressure of an Hb solution exceeds a physiological value when the Hb concentration is 5% or more;
2) to suppress the side effects by encapsulating hemoglobin having high physiological activity in membrane;
3) to retain various phosphate compounds or a glycolysis/reductase system for maintaining Hb functions such as oxygen affinity and stability of an oxygen complex in the same system; and
4) to have an advantage that a hemocyte dispersed system, which is a non-Newtonian fluid, shows a physiological function by distinctive flow form when circulating it in the body (particularly peripheral blood vessels).

Considering such primary roles of erythrocyte structure, it is clear that a dispersion system containing particles formed by encapsulating Hb in a capsule is suitable as the oxygen infusion.

On the other hand, it has been discovered that a phospholipid that is a biological component forms a vesicle structure independently, and many institutes have made studies on a hemoglobin vesicle since Djordjevich and Miller started researches on a hemoglobin vesicle using a liposome composed of phospholipid/cholesterol/fatty acid. The use of the hemoglobin vesicle has advantages in that 1) natural hemoglobin can be used without treatment, 2) the side effects caused by hemoglobin can be suppressed, 3) the viscosity, colloid osmotic pressure, or oxygen affinity can be adjusted to an arbitrary value, and 4) the retention time of blood in the body can be extended.

Various researches have been done for a liposome-encapsulated hemoglobin in which hemoglobin is encapsulated inside the layer of a liposome composed of lipid bilayer membrane (JP 52-151718, JP 58-183625, and JP 61-37735). However, a suspension of such a liposome-encapsulated hemoglobin has an extremely low colloid osmotic pressure, so that the effect of maintaining or increasing the circulating blood amount cannot be expected even when the suspension is administered to the blood vessel of a living body.

As alternatives to overcome the aforementioned defects, there has been disclosed artificial blood having both an oxygen carrying ability and a plasma expanding effect, which is formed by suspending a liposome-encapsulated hemoglobin in an aqueous solution of a plasma expander (U.S. Pat. No. 4,133,874 and JP 4-5242).

However, for the artificial blood disclosed in U.S. Pat. No. 4,133,874, the liposome-encapsulated hemoglobin tends to aggregate in the aqueous solution of the plasma expander. Therefore, the viscosity of the suspension becomes high, so that the suspension has difficulty in intravenous administration and there is a danger of the liposome aggregates causing embolization in a blood vessel.

In order to suppress an interaction between a hemoglobin vesicle and a protein in blood, the artificial blood disclosed in JP 4-5242 suppresses an interaction between a hemoglobin vesicle and a plasma expander by using an oxygen carrier in which PEG is bound to the hemoglobin vesicle surface (i.e., phospholipid) (JP 2-149512 or JP 3-218309).

However, it is known that when a water-soluble polymer such as PEG (synonymous with polyoxyethylene) is bound to a diacyl phospholipid such as phosphatidylethanolamine that is a major cell membrane component of a general living organism, the diacyl phospholipid bound to the water-soluble polymer is desorbed from a phospholipid bilayer membrane vesicle (J. R. Silvius and M. J. Zuckermann. *Biochemistry*, 32, 3153, 1993 and JP 2001-64383, paragraph 0004).

A pharmaceutical composition containing the aforementioned artificial oxygen carrier had the following problems. The administration of the composition to a living body without providing a colloid osmotic pressure causes a shock symptom. Moreover, in the case where the electrolyte balance differs from a physiological electrolyte balance, hemolysis or angiitis is caused due to angialgia when the pharmaceutical composition is administered to the living body or a difference between the crystalloid osmotic pressures. In addition, when the pH of the artificial oxygen infusion is higher than physiological pH, alkalosis is easily caused, whereas when the pH of the artificial oxygen infusion is lower than physiological pH, acidosis is easily caused.

SUMMARY OF THE INVENTION

An object of the present invention is to provide a pharmaceutical composition that has high oxygen carrying efficiency; and has a required colloid osmotic pressure, an appropriate crystalloid osmotic pressure, pH, and electrolyte balance.

The inventors of the present invention have made an extensive study to achieve the aforementioned object. As a result, the inventors of the present invention have found that the object can be achieved by a pharmaceutical composition prepared by appropriately adding at least one substance selected from the group consisting of a compound capable of providing an colloid osmotic pressure, an electrolyte, a saccharide, an amino acid, an antioxidant, a pH adjuster, and an isotonizing agent to a liposome-encapsulated hemoglobin preparation in which hemoglobin is encapsulated in a liposome, and the present invention has been completed. In addition, the inventors of the present invention have focused on the fact that a solution of a preparation including a conjugate of a metal complex having a porphyrin structure and albumin has a colloid osmotic pressure, which is incorporated in the present invention.

That is, the present invention relates to the following items:

(1) a pharmaceutical composition characterized by including an artificial oxygen carrier capable of adsorbing and desorbing oxygen reversibly in a living body and further including at least one substance selected from the group consisting of a compound capable of proving an colloid osmotic pressure, an electrolyte, a saccharide, an amino acid, an antioxidant, a pH adjuster, and an isotonizing agent;

(2) a pharmaceutical composition characterized by including an artificial oxygen carrier capable of adsorbing and desorbing oxygen reversibly in a living body and a compound capable of providing a colloid osmotic pressure;

(3) the pharmaceutical composition according to item (1) or (2), in which the artificial oxygen carrier is composed of a liposome-encapsulated hemoglobin;

(4) the pharmaceutical composition according to item (1) or (2), in which the artificial oxygen carrier is composed of a conjugate of a metal complex having a porphyrin structure and a protein;

(5) the pharmaceutical composition according to item (1) or (2), in which the artificial oxygen carrier is composed of a conjugate of a metal complex having a porphyrin structure and a protein and of a liposome-encapsulated hemoglobin;

(6) the pharmaceutical composition according to item (3) or (5), in which the liposome contains a conjugate of a non-phospholipid lipid and a polyalkylene glycol;

(7) the pharmaceutical composition according to item (3) or (5), in which the hemoglobin is a recombinant hemoglobin;

(8) the pharmaceutical composition according to item (4) or (5), in which the metal complex is an iron (II) complex and the protein is albumin;

(9) the pharmaceutical composition according to item (4) or (5), in which the protein is a recombinant protein;

(10) the pharmaceutical composition according to item (1) or (2), in which the composition is a liquid having a colloid osmotic pressure of about 1 to 50 mmHg, a crystalloid osmotic pressure of about 50 to 500 milliosmoles (mOsm), P50 of about 1 to 50 Torr, and pH of about 5.6 to 8.0;

(11) the pharmaceutical composition according to item (1) or (2), in which the composition supplies oxygen to an ischemic site or a tumor tissue;

(12) the pharmaceutical composition according to item (1) or (2), in which the composition is used for blood infusion when bleeding occurs; and (13) the pharmaceutical composition according to item (1) or (2), in which the composition is used in an organ storage perfusion solution, an extracorporeal circulation solution, or a cell culture solution.

DETAILED DESCRIPTION OF THE INVENTION

A pharmaceutical composition of the present invention includes, but is not limited to, a composition having a liquid, solid, or gel form. Among those, preferable is a composition having a liquid form.

Specific examples of the artificial oxygen carrier include a liposome-encapsulated hemoglobin, a conjugate of a metal complex having a porphyrin structure and albumin, or a mixture or conjugate thereof.

The metal complex having a porphyrin structure refers to a metal complex in which a central metal coordinates with a porphyrin ring and includes all compounds having a reversible binding ability to oxygen. The central metal of the metal complex is preferably iron, cobalt, or chromium; more preferably, iron (II) or cobalt (II).

The liposome-encapsulated hemoglobin (hereinafter abbreviated to HbV) refers to a compound in which hemoglobin is encapsulated in a liposome.

The term "liposome" typically refers to a closed vesicle that is formed of lipids membranously gathered and an aqueous phase inside thereof. However, in the present invention, the term particularly refers to all fine particles formed of gathered lipids regardless of whether or not the liposome has the aqueous phase inside there. Meanwhile, the structure of the liposome of the present invention is also not particularly limited, but may be a multilayer liposome or a monolayer liposome.

The size of the liposome of the present invention is not particularly limited, but the liposome may have a volume average particle size of about 10 to 5,000 nm, preferably about 30 to 500 nm. The volume average particle size of the liposome can be determined based on a principle such as a principle of dynamic light scattering.

The lipid forming the liposome of the present invention is not particularly limited, and may be a known lipid. Examples of the lipid include a glycolipid, sterols, a fatty acid, a phospholipid, an amphipathic alkyl amino acid derivative, a dialkyldimethylammonium, a polyglycerol alkyl ether, a polyoxyethylene alkyl ether, or the like (Liposome Technology, 2nd edition, vol. 1, 141, 1993), an amphipathic block copolymer such as a polyoxyethylene-polylactic acid block copolymer (JP 6-508831 B), long-chain alkylamines (such as tetradecylamine, hexadecylamine, and stearylamine), and long-chain fatty acid hydrazides (such as hydrazide myristate, hydrazide palmitate, and hydrazide stearate).

Examples of the glycolipid include a glyceroglycolipid and a sphingoglycolipid. Examples of the glyceroglycolipid include digalactosyl diglycerides (such as digalactosyl dilauroyl glyceride, digalactosyl dimyristoyl glyceride, digalactosyl dipalmitoyl glyceride, and digalactosyl distearoyl glyceride) and galactosyl diglycerides (such as galactosyl dilauroyl glyceride, galactosyl dimyristoyl glyceride, galactosyl dipalmitoyl glyceride, and galactosyl distearoyl glyceride). Examples of the sphingoglycolipid include galactosyl cerebroside, lactosyl cerebroside, and ganglioside.

Examples of the sterols include cholesterol, cholesterol hemisuccinate, 3β-[N—(N', N'-dimethylaminoethane)carbamoyl]cholesterol, ergosterol, and lanosterol.

In the present invention, those lipids may be used singly or in combination of two or more thereof.

Examples of the phospholipid include natural or synthetic phospholipids such as phosphatidylcholine, phosphatidylethanolamine, phosphatidylserine, phosphatidic acid, phosphatidylglycerol, phosphatidylinositol, lisophosphatidylcholine, sphingomyelin, egg yolk lecithin, soybean lecithin, and a hydrogenated phospholipid.

The liposome of the present invention is particularly preferably composed of a conjugate formed by binding a non-phospholipid lipid to a polyalkylene glycol.

The polyalkylene glycol is not particularly limited, but is preferably a compound having an alkylene chain with about 2 to 6 carbon atoms. Moreover, the alkylene chain may be substituted by a substituent, which is not detrimental to the present invention, such as a hydroxyl group, a carboxyl group, an amino group, and an alkoxy group. Specifically, PEG and polypropylene glycol can be used, for example. Among those, PEG can particularly preferably be used. The molecular weight of the polyalkylene glycol to be used is not particularly limited, but may be a number average molecular weight of about 200 to 4,000,000, preferably about 1,000 to 50,000. Particularly preferably, PEG has the aforementioned molecular weight when PEG is used.

In the present invention, the polyalkylene glycol content is not particularly limited, but is preferably about 0.1 to 30 mol % relative to the total amount of lipids composing a liposome.

The hemoglobin to be used in the present invention is not particularly limited, and may include hemoglobin derived from various living bodies and recombinant hemoglobin. Preferable is the recombinant hemoglobin.

Examples of the conjugate of a metal complex having a porphyrin structure and albumin include an oxygen infusion in which a tetraphenylporphyrin iron derivative such as 2-[8-{N-(2-methylimidazolyl)}octanoyloxymethyl]-5,10,15,20-tetrakis (α,α,α,α-o-pivaloylamino)phenylporphinato iron (II) is included in a hydrophobic pocket of human-derived albumin or recombinant albumin (referred to as albumin-heme) (E. Tsuchida, et al., Bioconjugate Chemistry. vol. 8., 534-538, 1997).

Examples of the metal complex having a porphyrin structure to be used in the present invention include, but are not particularly limited to, tetraphenylporphyrin, protoporphyrin, octaalkylporphyrin, and derivatives thereof. Preferable is a protoporphyrin derivative.

Examples of the albumin to be used in the present invention include, but are not particularly limited to, human serum albumin, animal-derived serum albumin, recombinant animal serum albumin, recombinant human serum albumin (rHSA), and multimers thereof. From the viewpoint of infection prevention or the like, particularly preferable is rHSA.

In the present invention, the term "P50" refers to an oxygen partial pressure in the case where a rate of hemoglobin binding to oxygen is 50%. The adjustment of P50 to 1 to 50 Torr can yield an oxygen carrier having a normal oxygen adsorbing and desorbing ability in a living body.

When the pharmaceutical composition of the present invention contains no compound capable of providing a colloid osmotic pressure, the colloid osmotic pressure is about 0 mmHg, whereas when the pharmaceutical composition of the present invention contains a compound capable of providing a colloid osmotic pressure (including a conjugate of a metal complex having a porphyrin structure and a protein), adverse effects on a living body can be prevented by adjusting the colloid osmotic pressure to about 1 to 50 mmHg. In addition, the pharmaceutical composition of the present invention has a crystalloid osmotic pressure of about 50 to 5,000 mOsm, preferably about 50 to 500 mOsm. Moreover, the pharmaceutical composition of the present invention preferably has a pH of about 5.6 to 8.0.

The compound capable of providing a colloid osmotic pressure of the present invention may include various polymers to be used for medicinal purposes as far as it has a colloid osmotic pressure. Examples of the compound include a dextran (e.g., a low-molecular-weight dextran), a dextran derivative (e.g., carboxymethyl dextran, carboxydextran, cationic dextran, and dextran sulfate), hydroxyethyl starch, hydroxypropyl starch, gelatin (e.g., modified gelatin), albumin (e.g., human plasma, human serum albumin, heated human plasma protein, and recombinant human serum albumin), PEG, polyvinyl pyrrolidone, carboxymethylcellulose, acacia gum, glucose, a dextrose (e.g., glucose monohydrate), oligosaccharides (e.g., oligosaccharide), a polysaccharide degradation product, an amino acid, and a protein degradation product. Among those, particularly preferable are low-molecular-weight dextran, hydroxyethyl starch, modified gelatin, and recombinant albumin.

The electrolyte to be used in the present invention typically includes various electrolytes to be used for medicinal purposes. Examples of the electrolyte include sodium salts (e.g., sodium chloride, sodium hydrogen carbonate, sodium citrate, sodium lactate, sodium sulfate, sodium dihydrogen phosphate, disodium hydrogen phosphate, sodium acetate, sodium glycerophosphate, sodium carbonate, an amino acid sodium salt, sodium propionate, sodium β-hydroxybutyrate, and sodium gluconate), potassium salts (e.g., potassium chloride, potassium acetate, potassium gluconate, potassium hydrogen carbonate, potassium glycerophosphate, potassium sulfate, potassium lactate, potassium iodide, potassium dihydrogen phosphate, dipotassium hydrogen phosphate, potassium citrate, an amino acid potassium salt, potassium propionate, and potassium β-hydroxybutyrate), calcium salts (e.g., calcium chloride, calcium gluconate, calcium lactate, calcium glycerophosphate, calcium pantothenate, and calcium acetate), magnesium salts (e.g., magnesium chloride, magnesium sulfate, magnesium glycerophosphate, magnesium acetate, magnesium lactate, and an amino acid magnesium salt), ammonium salts (e.g., ammonium chloride), zinc salts (e.g., zinc sulfate, zinc chloride, zinc gluconate, zinc lactate, and zinc acetate), iron salts (e.g., iron sulfate, iron chloride, and iron gluconate), copper salts (e.g., copper sulfate), and manganese salts (for example, manganese sulfate). Among those, particularly preferable are sodium chloride, potassium chloride, magnesium chloride, disodium hydrogen phosphate, dipotassium hydrogen phosphate, potassium dihydrogen phosphate, sodium lactate, sodium acetate, sodium citrate, potassium acetate, potassium glycerophosphate, calcium gluconate, calcium chloride, magnesium sulfate, and zinc sulfate.

The saccharides to be used in the present invention typically include various saccharides to be used for medicinal purposes. Examples of the saccharides include glucose, fructose, xylitol, sorbitol, mannitol, dextrin, glycerin, sucrose, trehalose, glycerol, maltose, lactose, and erythritol. Among those, particularly preferable are glucose, fructose, xylitol, sorbitol, mannitol, dextrin, glycerin, and sucrose.

The amino acid to be used in the present invention typically includes various amino acids to be used for medicinal purposes and salts thereof. Examples thereof include lysine, lysine hydrochloride, lysine acetate, asparagine, glutamine, aspartic acid, glutamic acid, serine, threonine, tyrosine, methionine, cystine, cysteine, cysteine hydrochloride, cysteine malate, homocysteine, isoleucine, leucine, phenylalanine, tryptophan, valine, arginine, arginine hydrochloride, histidine, histidine hydrochloride, alanine, proline, aminoacetic acid, and salts thereof. Among those, particularly preferable are lysine, asparagine, glutamine, aspartic acid, glutamic acid, serine, threonine, tyrosine, methionine, cystine, cysteine, homocysteine, and aminoacetic acid.

The antioxidant to be used in the present invention typically includes various antioxidants to be used for medicinal purposes. Examples of the antioxidant include sodium hydrogen sulfite, sodium sulfite, sodium pyrosulfite (e.g., sodium metabisulfite), rongalite (CH2OHSO2Na), ascorbic acid, sodium ascorbate, erythorbic acid, sodium erythorbate, cysteine, cysteine hydrochloride, homocysteine, glutathione, thioglycerol, α-thioglycerin, sodium edetate, citric acid, isopropyl citrate, potassium dichloroisocyanurate, sodium thioglycolate, sodium pyrosulfite 1,3-butylene glycol, disodium calcium ethylenediaminetetraacetate, disodium ethylenediaminetetraacetate, an amino acid sulfite (e.g, L-lysine sulfite), butylhydroxyanisole (BHA), butylhydroxytoluene (BHT), propyl gallate, ascorbyl palmitate, vitamin E and derivatives thereof (e.g., dl-α-tocopherol, tocopherol acetate, natural vitamin E, d-δ-tocopherol, mixed tocopherol, and trolox), guaiac, nordihydroguaiaretic acid (NDGA), L-ascorbate stearate esters, soybean lecithin, palmitic acid ascorbic acid, benzotriazol, and pentaerythrityl-tetrakis[3-(3,5-di-t-butyl-4-hydroxyphenyl)propionate]2-mercaptobenzimidazole. Among those, preferable are sodium hydrogen sulfite, sodium sulfite, ascorbic acid, homocysteine, dl-α-tocopherol, tocopherol acetate, glutathione, and trolox.

The pH adjuster to be used in the present invention typically includes various pH adjusters to be used for medicinal purposes. Examples of acidic pH adjusters include adipic acid, sodium caseinate, hydrochloric acid, diluted hydrochloric acid, sulfuric acid, aluminum potassium sulfate, citric acid, sodium dihydrogen citrate, glycine, glucono-δ-lactone, gluconic acid, sodium gluconate, crystal sodium dihydrogen phosphate, succinic acid, acetic acid, ammonium acetate, tartaric acid, D-tartaric acid, lactic acid, glacial acetic acid, monosodium fumarate, sodium propionate, boric acid, ammonium borate, maleic acid, malonic acid, malic acid, anhydrous disodium phosphate, methanesulfonic acid, phosphoric acid, and dihydrogen phosphates (e.g., potassium dihydrogen phosphate and sodium dihydrogen phosphate). Among those, preferable are hydrochloric acid, citric acid, succinic acid, acetic acid, lactic acid, glacial acetic acid, phosphoric acid, potassium dihydrogen phosphate, and sodium dihydrogen phosphate.

Examples of alkaline pH adjusters include aqueous ammonia, dry sodium carbonate, sodium citrate, sodium acetate, diisopropanolamine, sodium L-tartrate, lactates (e.g., calcium lactate and sodium lactate), borax, sodium maleate, sodium malonate, sodium malate, potassium hydroxide, calcium hydroxide, sodium hydroxide, magnesium hydroxide, sodium hydrogen carbonate, sodium carbonate, triisopropanolamine, monoethanolamine, triethanolamine, anhydrous sodium acetate, anhydrous sodium monohydrogen phosphate, meglumine, phosphates (e.g., trisodium phosphate), sodium salts of barbital, and hydrogen phosphates (e.g., disodium hydrogen phosphate and dipotassium hydrogen phosphate). Among those, particularly preferable are sodium acetate, sodium hydroxide, sodium hydrogen carbonate, sodium carbonate, trisodium phosphate, disodium hydrogen phosphate, and dipotassium hydrogen phosphate.

The pH of the pharmaceutical composition of the present invention may be adjusted by bubbling of carbon dioxide gas.

The isotonizing agent to be used in the present invention typically includes various isotonizing agents to be used for medicinal purposes. Examples of the isotonizing agent include aminoethylsulfonic acid, sodium hydrogen sulfite, potassium chloride, calcium chloride, sodium chloride, benzalkonium chloride, magnesium chloride, saccharides (e.g., lactose, concentrated glycerin, glucose, fructose, xylitol, and glycerin), sugar alcohols (e.g., D-sorbitol and D-mannitol), citric acid, sodium citrate, crystal sodium dihydrogen phosphate, calcium bromide, sodium bromide, sodium hydroxide, physiological saline, sodium tartrate dihydrate, sodium hydrogen carbonate, nicotinamide, sodium lactate solutions, propylene glycol, benzyl alcohol, boric acid, borax, anhydrous sodium pyrophosphate, phosphoric acid, disodium hydrogen phosphate, potassium dihydrogen phosphate, sodium dihydrogen phosphate, and macrogol 4000. Among those, particularly preferable are potassium chloride, sodium chloride, concentrated glycerin, disodium hydrogen phosphate, and potassium dihydrogen phosphate.

The method of producing the pharmaceutical composition of the present invention may include various known methods.

The method of preparing the liposome-encapsulated hemoglobin may be any known method such as a reverse phase evaporation method, a high-pressure extrusion method, and a method using a microfluidizer. In order to prevent denaturation of hemoglobin, the preparation of the liposome-encapsulated hemoglobin is preferably performed at a low temperature of 10° C. or less.

In addition, the method of preparing the conjugate of a metal complex having a porphyrin structure and a protein may be selected among various known methods. Examples of the method include a method of preparing an albumin-heme described in E. Tsuchida et al., Bioconjugate Chemistry, vol. 8, 534-538, 1997.

The liposome to be used in the present invention can be produced in accordance with various known methods. When producing a liposome containing a conjugate of a polyalkylene glycol and a lipid, the polyalkylene glycol typically binds to the lipid via a spacer molecule. The spacer molecule is not particularly limited as long as it can bind to both a polyalkylene glycol and a lipid. Examples of the spacer molecule include an amino acid and succinic acid. A particularly preferable amino acid is a trifunctional amino acid that has one reactive functional group in the core part and has reactive functional groups in the respective two branched terminals. Examples of the amino acid include lysine, asparagine, glutamine, aspartic acid, glutamic acid, serine, threonine, and tyrosine. Among those, more preferable is a trifunctional amino acid that has a first reactive functional group in the core part and has the same second functional group in the respective two branched terminals (such as lysine, glutamine, or asparagine that has one terminal carboxyl group and two terminal amino groups; or such as aspartic acid or glutamic acid that has one terminal amino group and two terminal carboxyl groups).

The hemoglobin to be used in the present invention is desirably prepared by removing stroma from a human erythrocyte, and the pH of a hemoglobin solution is desirably adjusted to 7.0 to 7.5. For adjusting the pH of the hemoglobin solution, an aqueous solution of sodium hydroxide, sodium carbonate, or sodium hydrogen carbonate may be used. The pH adjustment can also be performed by adding a buffer to the hemoglobin solution. Examples of the buffer include Tris, bis-Tris, HEPES, and a buffer of inorganic phosphates or the like. The recombinant hemoglobin can also be prepared in the same manner as above.

The pharmaceutical composition of the present invention can be applied in all fields where oxygen carriers are required. For example, the composition can be administered to a living body for supplying oxygen to an ischemic site or a tumor tissue or for blood infusion when bleeding occurs. Alternatively, the composition can be used as an organ storage perfusion solution, as extracorporeal circulation solution, or as a cell culture solution.

EXAMPLES

Hereinafter, the present invention will be described in more detail by way of examples, but the present invention is not limited to the examples.

Example 1

Homocysteine (hereinafter abbreviated to Hcy) and about a three-fold molar amount (relative to Hb) of a pyridoxal 5'-phosphate (hereinafter abbreviated to PLP) solution (solvent: an NaOH aqueous solution) were added to a Hb solution ([Hb]: 40 g/dL). Subsequently, the mixture was adjusted to pH 7.4 and stirred at 4° C. overnight, and the resultant mixture was filtered using a 0.22 μm-filter (final concentrations: Hb: 5.9 mmol/L, PLP: 17.3 mmol/L, and Hcy: 5 mmol/L). The Hb in the filtrate was carbon-monoxided by repeating deaeration and CO gas flow of the filtrate three times, to thereby yield a carbon-monoxided Hb solution.

Meanwhile, a mixture of DPPC/cholesterol/1,5-dipalmitoyl-L-glutamate-N-succinic acid=10/10/2 (molar ratio) was weighed in a total amount of 20 g, and dissolved in benzene. The mixture was mixed and freeze-dried, to thereby yield lipid-mixed powder in which lipids are uniformly dispersed. The lipid-mixed powder was hydrated by adding the powder to the carbon-monoxided Hb solution by portions at 4° C., followed by stirring overnight. Subsequently, the average diameter of the powder was adiusted to 0.22 μm using an extruder (manufactured by LIFEX BIOMEMBRANES, INC.), to thereby yield an HbV dispersion.

Four-fold amount of physiological saline was added to the HbV dispersion, and ultrafiltration (molecular weight: 1,000, 000) was repeated several times using a Pellicon holder (manufactured by Millipore Corporation) to remove Hb in the external aqueous phase. At that time, it was confirmed that the external aqueous phase turned transparent. Subsequently, a conjugate in which PEG binds to distearyl glutaryl ester (hereinafter abbreviated to PEG-DSGE) was dissolved in physioloqical saline so as to have a PEG-DSGE concentration ratio of 0.3 mol % relative to the total lipid mass. Subsequently, the lipid concentration was adjusted to 2.0 g/dL with physiological saline. A PEG-DSGE aqueous solution was added dropwise by portions to the HbV dispersion. The mixture was stirred and mixed under a CO atmosphere for 2 hours (37° C., 400 rpm) and further stirred and mixed overnight at 4° C.

After completion of the stirring, the Hb concentration was adjusted to 2.0 g/dL with physiological saline, and the mixture was then subjected to oxygen flow and visible light irradiation for desorption of CO from Hb. The resultant mixture was concentrated by centrifugation, to thereby yield an HbV pellet layer in the lower layer.

Phosphate buffer saline (hereinafter abbreviated to PBS) was added to the HbV pellet layer, and ultracentrifugation was performed for washing. Recombinant human serum albumin (hereinafter abbreviated to rHSA) was dissolved in PBS so as to have an rHSA concentration of 5%, and the solution was added to the lower layer, to thereby yield 200 mL of HbV solution ([Hb]: 10 g/dL, about pH 7.4).

The resultant solution had a colloid osmotic pressure of about 20 mmHg and a crystalloid osmotic pressure of about 300 mOsm.

Moreover, the solution was found to have a maximum absorption spectrum (Q band) at about 575 nm. After the dispersion was aerated with nitrogen gas, the solution was found to have a maximum absorption spectrum (Q band) at about 555 nm corresponding to that of a deoxyhemoglobin, so that it was confirmed that oxygen was adsorbed and desorbed reversibly. In addition, the deoxyhemoglobin was aerated with mixed gas having different oxygen partial pressures stepwise to determine an oxygen affinity at 37° C. As a result, the solution was found to have P50 of about 32 Torr.

Example 2

Hcy and an equal molar amount (relative to Hb) of a PLP solution (solvent: an NaOH aqueous solution) were added to a Hb solution ([Hb]: 40 g/dL). Subsequently, the mixture was adjusted to pH 7.4 and stirred at 4° C. overnight, and the resultant mixture was filtered using a 0.22 μm-filter (final concentrations: Hb: 5.9 mmol/L, PLP: 5.9 mmol/L, and Hcy: 5 mmol/L). The Hb in the filtrate was carbon-monoxided by repeating deaeration and CO gas flow of the filtrate three times, to thereby yield a carbon-monoxided Hb solution.

Meanwhile, a mixture of dipalmitoylphosphatidylcholine hereinafter abbreviated to DPPC)/cholesterol/dipalmitoylphosphatidylglycerol (hereinafter abbreviated to DPPG) =10/10/2 (molar ratio) was weighed in a total amount of 20 g, and dissolved in benzene. Subsequently, the mixture was freeze-dried, to thereby yield lipid-mixed powder in which lipids are uniformly dispersed. The lipid-mixed powder was hydrated by adding the powder to the carbon-monoxided Hb solution by portions at 4° C., followed by stirring overnight. Subsequently, the diameter of the powder was adjusted to 0.22 μm using an extruder (manufactured by LIPEX BIOMEMBRANES, INC.), to thereby yield an HbV dispersion.

Four-fold amount of physiological saline was added to the HbV dispersion, and ultrafiltration (molecular weight: 1,000,000) was repeated several times using a Pellicon holder (manufactured by Millipore Corporation) to remove Hb, which had not been encapsulated in endoplasmic reticulum, in the external aqueous phase. At that time, it was confirmed that the external aqueous phase turned transparent. Subsequently, the lipid concentration was adjusted to 2.0 g/dL with physiological saline. On the other hand, a conjugate formed by binding PEG and distearoylphosphatidylethanolamine via succinic acid (PEG-DSPE) was dissolved in physiological saline so as to have a PEG-DSPE content of 0.3 mol % relative to the total lipid amount, to thereby prepare a PEG-DSPE aqueous solution. The PEG-DSPE aqueous solution was added dropwise by portions to the HbV dispersion. The mixture was stirred and mixed under a CO atmosphere for 2 hours (37° C., 400 rpm) and further stirred and mixed overnight at 4° C.

After completion of the stirring, the Hb concentration was adjusted to 2.0 g/dL with physiological saline, and the mixture was then subjected to oxygen flow and visible light irradiation for desorption of CO from Hb. The resultant mixture was concentrated by centrifugation, to thereby yield an HbV pellet layer in the lower layer.

PBS was added to the HbV pellet layer, and ultracentrifugation was performed for washing. Then, rHSA was dissolved in PBS so as to have an rHSA concentration of 5%, and the solution was added to the lower layer, to thereby yield 200 mL of HbV solution ([Hb]: 10 g/dL, about pH 7.4).

The resultant solution had a colloid osmotic pressure of about 20 mmHg and a crystalloid osmotic pressure of about 300 mOsm.

Moreover, the solution was found to have a maximum absorption spectrum (Q band) at about 575 nm. After the dispersion was aerated with nitrogen gas, the solution was found to have a maximum absorption spectrum (Q band) at about 555 nm corresponding to that of a deoxyhemoglobin, so that it was confirmed that oxygen was adsorbed and desorbed reversibly. In addition, the deoxyhemoglobin was aerated with mixed gas having different oxygen partial pressures stepwise to determine an oxygen affinity at 37° C. As a result, the solution was found to have P50 of about 18 Torr.

Example 3

Three-fold molar amount (relative to Hb) of a PLP solution (solvent: an NaOH aqueous solution) was added to a Hb solution ([Hb]: 40 g/dL). Subsequently, the mixture was adjusted to pH 7.4 and stirred at 4° C. overnight, and the resultant mixture was filtered using a 0.22 μm-filter (final concentrations: Hb: 5.9 mmol/L, PLP: 17.3 mmol/L, and Hcy: 5 mmol/L). The Hb in the filtrate was carbon-monoxided by repeating deaeration and CO gas flow of the filtrate three times, to thereby yield a carbon-monoxided Hb solution.

Meanwhile, a mixture of DPPC/cholesterol/1,5-dipalmitoyl-L-glutamate-N-succinic acid=10/10/2 (mol ratio) was weighed in a total amount of 20 g, and dissolved in benzene. Subsequently, a conjugate in which PEG is bound to distearyl glutaryl ester (hereinafter abbreviated to PEG-DSGE) was dissolved in physiological saline so as to have a PEG-DSGE concentration ratio of 0.3 mol % relative to the total lipid amount. The mixture was mixed and freeze-dried, to thereby yield lipid-mixed powder in which lipids were uniformly dispersed. The lipid-mixed powder was hydrated by adding the powder to the carbon-monoxided Hb solution by portions at 4° C., followed by stirring overnight. Subsequently, the diameter of the powder was adjusted to 0.22 μm using an extruder (manufactured by Lipex Biomembranes Inc), to thereby yield an HbV dispersion.

Four-fold amount of physiological saline was added to the HbV dispersion, and ultrafiltration (molecular weight: 1,000,000) was repeated a few times using a Pellicon holder (manufactured by Millipore Corporation) to remove Hb in the external aqueous phase. At that time, it was confirmed that the external aqueous phase turned transparent. Subsequently, the lipid concentration was adjusted to 2.0 g/dL with physiological saline. A PEG-DSGE aqueous solution was added dropwise by portions to the HbV dispersion. The mixture was stirred under a CO atmosphere for 2 hours (37° C., 400 rpm) and further stirred overnight at 4° C.

After completion of the stirring, the Hb concentration was adjusted to 2.0 g/dL with physiological saline, and the mixture was then subjected to oxygen flow and visible light irradiation for desorption of CO from Hb. The resultant mixture was concentrated by ultracentrifugation, to thereby yield an HbV pellet layer in the lower layer.

Physiological saline was added to the HbV pellet layer, and ultracentrifugation was performed for washing. Then, rHSA was dissolved in physiological saline so as to have an rHSA concentration of 5%, and the solution was added to the lower layer, to thereby yield 200 mL of an HbV solution ([Hb]: 8.6 g/dL, about pH 7.4).

The resultant solution had a colloid osmotic pressure of about 20 mmHg and a crystalloid osmotic pressure of about 300 mOsm.

Moreover, the solution was found to have a maximum absorption spectrum (Q band) at about 575 nm. After the dispersion was aerated with nitrogen gas, the solution was found to have a maximum absorption spectrum (Q band) at about 555 nm corresponding to that of a deoxyhemoglobin, so that it was confirmed that oxygen was adsorbed and desorbed reversibly. In addition, the deoxyhemoglobin was aerated with mixed gas having different oxygen partial pressures stepwise to determine an oxygen affinity at 37° C. As a result, the solution was found to have P50 of about 32 Torr.

Example 4

Hcy and an equal molar amount (relative to Hb) of a PLP solution (solvent: an NaOH aqueous solution) were added to a Hb solution ([Hb]: 40 g/dL). Subsequently, the mixture was adjusted to pH 7.4 and stirred at 4° C. overnight, and the resultant mixture was filtered using a 0.22 μm-filter (final concentrations: Hb: 5.9 mmol/L, PLP: 5.9 mmol/L, and Hcy: 5 mmol/L). The Hb in the filtrate was carbon-monoxided by repeating deaeration and CO gas flow of the filtrate three times, to thereby yield a carbon-monoxided Hb solution.

Meanwhile, a mixture of DPPC/cholesterol/DPPG=10/10/2 (mol ratio) was weighed in a total amount of 20 g, and dissolved in benzene. Subsequently, the mixture was freeze-dried, to thereby yield lipid-mixed powder in which lipids were uniformly dispersed. The lipid-mixed powder was hydrated by adding the powder to the carbon-monoxided Hb solution by portions at 4° C., followed by stirring overnight. Subsequently, the diameter of the powder was adjusted to 0.22 μm using an extruder (manufactured by Lipex Biomembranes Inc), to thereby yield an HbV dispersion.

Four-fold amount of physiological saline was added to the HbV dispersion, and ultrafiltration (molecular weight: 1,000,000) was repeated a few times using a Pellicon holder (manufactured by Millipore Corporation) to remove Hb, which had not been encapsulated in endoplasmic reticulum, in the external aqueous phase. At that time, it was confirmed that the external aqueous phase turned transparent. Subsequently, the lipid concentration was adjusted to 2.0 g/dL with physiological saline. On the other hand, a conjugate formed by binding PEG and distearoylphosphatidylethanolamine via succinic acid (PEG-DSPE) was dissolved in physiological saline so as to have a PEG-DSPE concentration ratio of 0.3 mol % relative to the total lipid amount, to thereby prepare a PEG-DSPE aqueous solution. The PEG-DSPE aqueous solution was added dropwise by portions to the HbV dispersion. The mixture was stirred under a CO atmosphere for 2 hours (37° C., 400 rpm) and further stirred overnight at 4° C.

After completion of the stirring, the Hb concentration was adjusted to 2.0 g/dL with physiological saline, and the mixture was then subjected to oxygen flow and visible light irradiation for desorption of CO from Hb. The resultant mixture was concentrated by ultracentrifugation, to thereby yield an HbV pellet layer in the lower layer.

Physiological saline was added to the HbV pellet layer, and ultracentrifugation was performed for washing. Then, recombinant human serum albumin (hereinafter abbreviated to rHSA) was dissolved in physiological saline so as to have an rHSA concentration of 5%, and the solution was added to the lower layer, to thereby yield 200 mL of an HbV solution ([Hb]: 8.6 g/dL, about pH 7.4).

The resultant solution had a colloid osmotic pressure of about 20 mmHg and a crystalloid osmotic pressure of about 300 mOsm.

Moreover, the solution was found to have a maximum absorption spectrum (Q band) at about 575 nm. After the dispersion was aerated with nitrogen gas, the solution was found to have a maximum absorption spectrum (Q band) at about 555 nm corresponding to that of a deoxyhemoglobin, so that it was confirmed that oxygen was adsorbed and desorbed reversibly. In addition, the deoxyhemoglobin was aerated with mixed gas having different oxygen partial pressures stepwise to determine an oxygen affinity at 37° C. As a result, the solution was found to have P50 of about 18 Torr.

Experimental Example 1

A resuscitation test from hemorrhagic shock was performed using the HbV solution prepared in Example 3 to evaluate the effect of the dispersion as a infusion having an oxygen carrying ability on the basis of the blood pressure and the gas composition in blood. A Wistar rat (male, about 250 g) was anesthetized by sevoflurane inhalation under spontaneous breathing, and the rat was intubated via carotid vein. Subsequently, 50% of circulating blood was removed via carotid. After the rat was allowed to stand for 15 minutes, a resuscitation solution was administered to the rat via carotid, followed by observation over 6 hours. The resuscitation solution used was a solution prepared by dispersing the HbV solution prepared in Example 3 in a 5% rHSA aqueous solution (hereinafter referred to as HbV/rHSA), a solution prepared by dispersing an HbV solution obtained in the same manner as in Example 3 in physiological saline (hereinafter referred to as HbV/saline), or the removed blood to which heparin was added.

Figure 1:
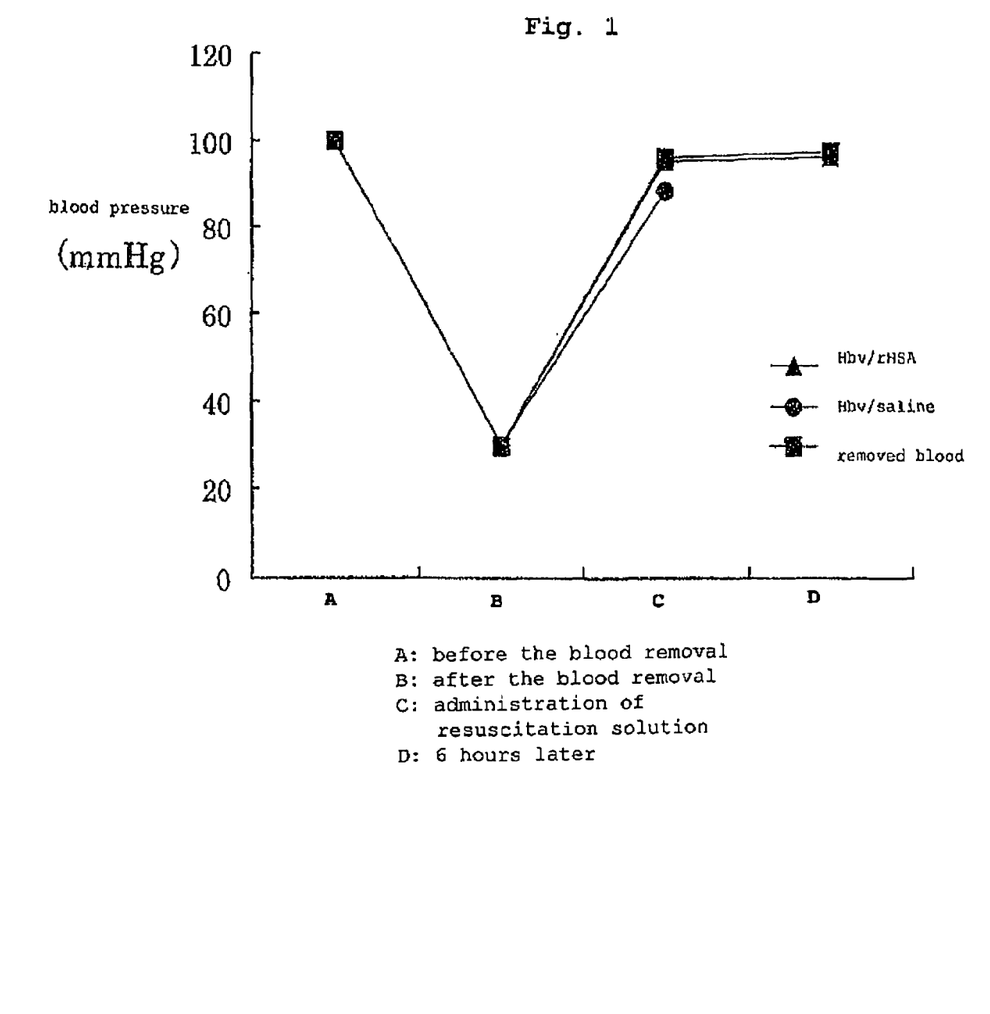
FIG. 1 A graph showing the improving effect of the present invention on decrease in blood pressure.
Figure 2:
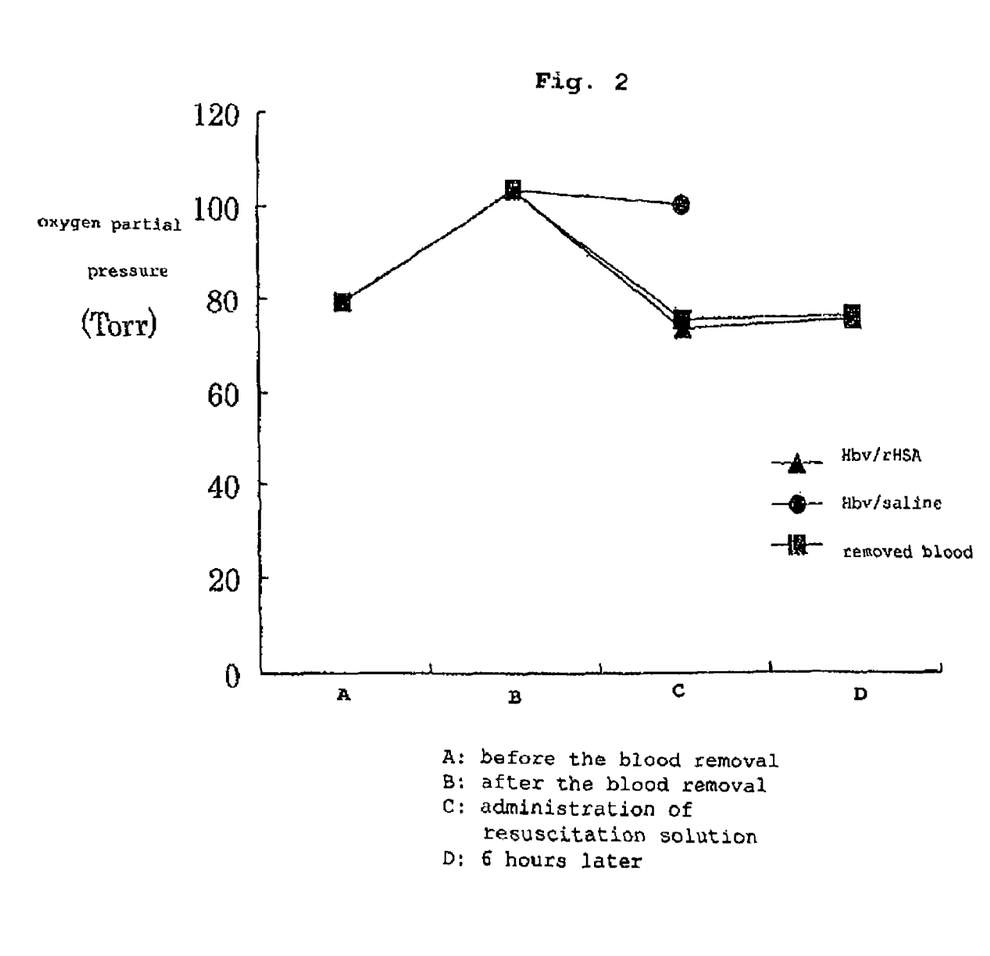
FIG. 2 A graph showing the improving effect of the present invention on increase in oxygen partial pressure in arterial blood.
Figure 3:
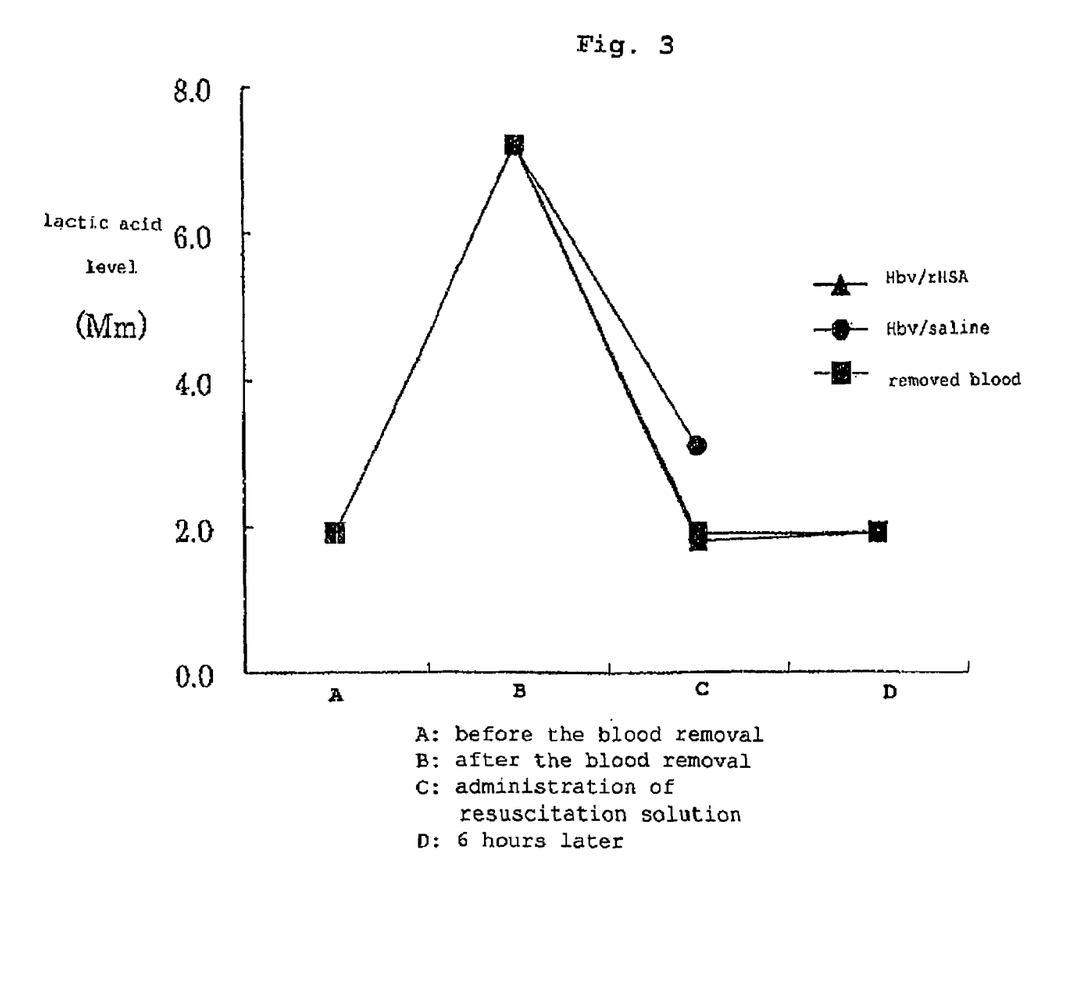
FIG. 3 A graph showing the improving effect of the present invention on the lactic acid level.

It was found that the blood pressure decreased from 100 mmHg before the blood removal to 30 mmHg after the blood removal (FIG. 1). The oxygen partial pressure in arterial blood (hereinafter referred to as PaO2) increased from 79 Torr to 103 Torr (FIG. 2). In addition, the lactic acid level significantly increased from 1.9 mM to 7.2 mM (FIG. 3). The blood pressure for the HbV/rHSA administered group recovered to 95 mmHg immediately after the administration, and the level was equivalent to that for the removed blood administered group and maintained for 6 hours (FIG. 1). Similarly, the gas composition in blood also recovered, and PaO2 and the lactic acid level were 73 Torr (FIG. 2) and 1.8 mM (FIG. 3), respectively. Meanwhile, for the HbV/saline administered group, the blood pressure recovered to 88 mmHg (FIG. 1) but the lactic acid level was 3.1 mM even after the administration, so that the two rats did not recover and died before completion of the observation over 6 hours.

HbV/rHSA had a colloid osmotic pressure of 20 Torr, while HbV/saline had a colloid osmotic pressure of 0 Torr.

The aforementioned results revealed that a plasma expander must be used in combination with an artificial oxygen carrier particularly when recovery of circulating blood amount is important, particularly at the time of resuscitation from hemorrhagic shock.

Example 5

A porphyrin-iron complex (2-[8-{N-(2-methylimidazolyl)}octanoyloxymethyl]-5,10,15,20-tetrakis ($\alpha,\alpha,\alpha,\alpha$-o-pivaloylamino) phenylporphinato iron (II)) was dissolved in ethanol. Subsequently, an L-ascorbic acid solution was added thereto for reduction of the central iron, and carbon monoxide gas was aerated to invert the porphyrin-iron complex into a carbon monoxide complex. The resultant mixture was added to recombinant human serum albumin diluted with a phosphate buffer, followed by mixing, to thereby include the porphyrin-iron complex in albumin. The mixture was concentrated by removing ethanol in the mixture by constant volume ultrafiltration dialysis using a phosphate buffer. The salt concentration of the resultant mixture was adjusted to 140 mM by adding sodium chloride thereto, to thereby yield a dispersion of a porphyrin-iron complex-albumin inclusion compound (pH 7.3, albumin concentration 5 w/v %). The dispersion had a colloid osmotic pressure of about 20 mmHg, and a crystalloid osmotic pressure of about 300 mOsm.

The dispersion was subjected to light irradiation with oxygen substitution in an ice bath to yield an oxyhemoglobin, and the resultant dispersion was found to have a maximum absorption spectrum at 421 nm. After the dispersion was aerated with nitrogen gas, the dispersion was found to have a maximum absorption spectrum at 441 nm corresponding to that of a deoxyhemoglobin. As a result, it was confirmed that oxygen was adsorbed and desorbed reversibly. In addition, the deoxyhemoglobin was aerated with mixed gas having different oxygen partial pressures stepwise to determine an oxygen affinity at 37° C. As a result, the dispersion was found to have P50 of 33 Torr.

Example 6

A porphyrin-iron complex (2-[8-{N-(2-methylimidazolyl)} octanoyloxymethyl]-5,10,15,20-tetrakis{$\alpha,\alpha,\alpha,\alpha$-o-(1-methylcyclohexanoyl)amino}phenilporphynato iron (II)) was dissolved in ethanol. Subsequently, an L-ascorbic acid solution was added thereto for reduction of the central iron, and carbon monoxide gas was aerated to invert the porphyrin-iron complex into a carbon monoxide complex. The resultant mixture was added to recombinant human serum albumin diluted with a phosphate buffer, followed by mixing, to thereby include the porphyrin-iron complex in albumin. The mixture was concentrated by removing ethanol in the mixture by constant volume ultrafiltration dialysis using a phosphate buffer (pH 7.3). The salt concentration of the resultant mixture was adjusted to 140 mM by adding sodium chloride thereto, to thereby yield a dispersion of a porphyrin-iron complex-albumin inclusion compound (pH 7.3, albumin concentration 5 w/v %). The dispersion had a colloid osmotic pressure of about 20 mmHg, and a crystalloid osmotic pressure of about 300 mOsm.

The dispersion was subjected to light irradiation with oxygen substitution in an ice bath to yield an oxyhemoglobin, and the resultant dispersion was found to have a maximum absorption spectrum at 424 nm. After the dispersion was aerated with nitrogen gas, the dispersion was found to have a maximum absorption spectrum at 443 nm corresponding to that of a deoxyhemoglobin. As a result, it was confirmed that oxygen was adsorbed and desorbed reversibly. In addition, the deoxyhemoglobin was aerated with mixed gas having different oxygen partial pressures stepwise to determine an oxygen affinity at 37° C. As a result, the dispersion was found to have P50 of 35 Torr.

Experimental Example 2

The porphyrin-iron complex-albumin inclusion compounds prepared in Examples 5 and 6 were evaluated for oxygen supplying ability to hypoxic cells and tissues. A Wister IGS male rat (body weight 275 to 315 g) was anesthetized by sevoflurane inhalation under spontaneous breathing, and a catheter was inserted to the rat via the right common carotid artery to prepare a route for blood removal and for arterial blood drawing. The left femoral region was dissected, and a catheter was inserted via the left femoral artery to prepare a route for measurement of blood pressure. The right femoral region was dissected, and a catheter was inserted via the right femoral artery to prepare a route for administration of a test substance or a control substance and for drawing venous blood. The belly was dissected, and an oxygen electrode (manufactured by Intermedical Inc., POE-40PS) was inserted into the renal cortex. Then, blood exchange of the rat was performed to exchange 70% of blood (relative to whole blood) of the rat with a 5% rHSA solution. After completion of the blood exchange, 30% of the estimated whole blood amount (converted as 56 mL/kg body weight) was removed via the right common carotid artery. Immediately after the blood removal, the rat was administered with an equal amount (relative to the removed blood amount) of the test substance (a dispersion of the porphyrin-iron complex-albumin inclusion compound prepared in Example 5 or 6) or a control substance (5% rHSA solution, retransfused blood of the removed blood). After that, observation was performed for 2 hours after the administration, and life or death was determined. The average blood pressure was measured by using a polygraph system (manufactured by NIHON KOHDEN CORPORATION, LEG-1000, Ver. 01-02) via an amplifier for pressure. By use of the oxygen electrode inserted into the renal cortex, the venous blood oxygen partial pressure was measured by using an apparatus for measuring tissue oxygen partial pressure (manufactured by Intermedical Inc., PO2-100DW)

Figure 4:
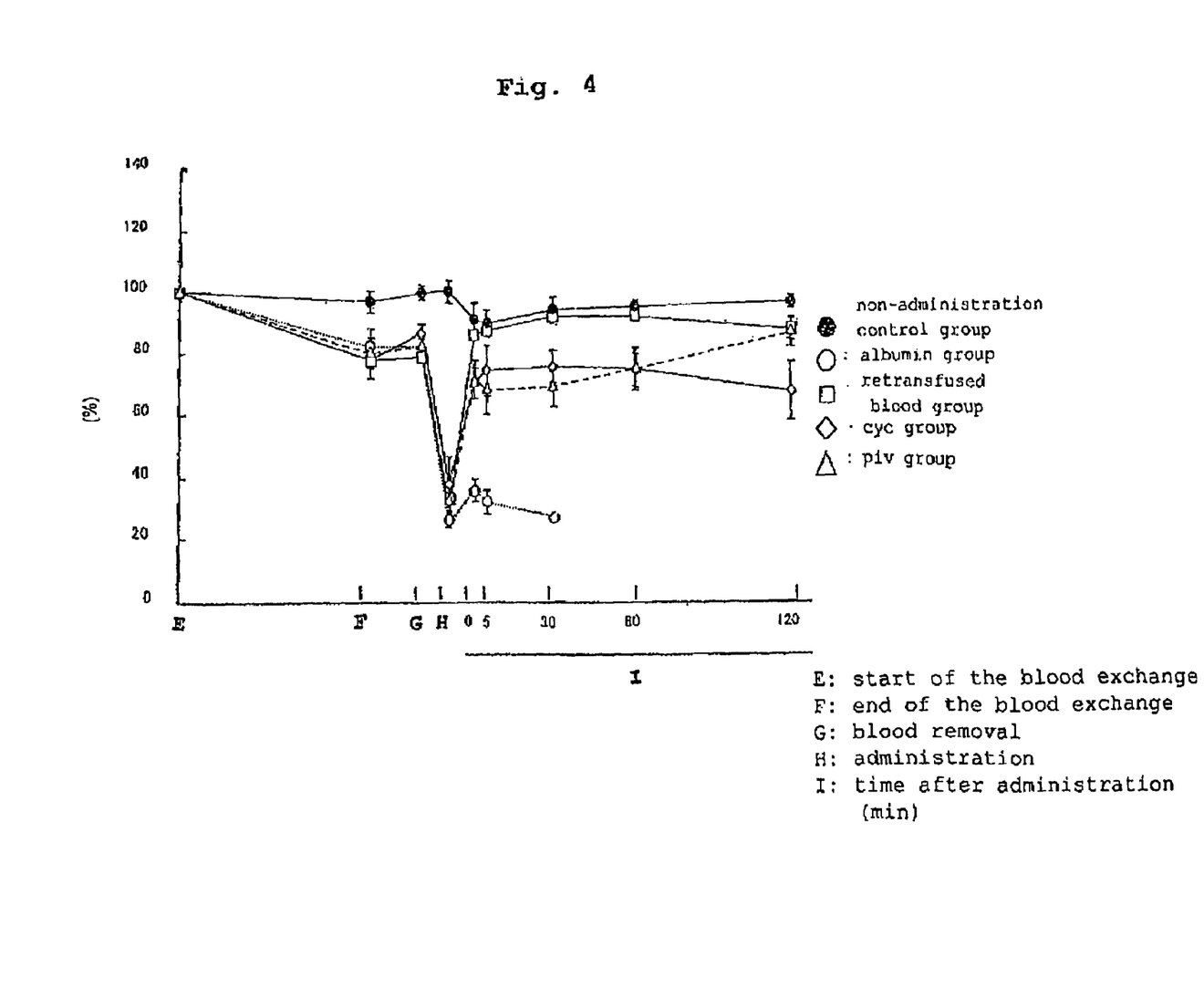
FIG. 4 A graph showing the improving effect of the present invention on decrease in blood pressure.

FIG. 4 shows the result of the measurement of the average blood pressure. The average blood pressure was measured for each of the albumin group, the retransfused blood group, the dispersion of the porphyrin-iron complex-albumin inclusion compound prepared in Example 5 (hereinafter referred to as piv group), and the dispersion of the porphyrin-iron complex-albumin inclusion compound prepared in Example 6 (hereinafter referred to as cyc group). The average blood pressure decreased to about 80% relative to the initial level by exchanging 70% of blood with the 5% rHSA solution. In addition, the average blood pressure decreased to about 25% by removing 30% of blood. After that, the blood pressure of the albumin group did not increase even when albumin was administered, while the blood pressure of the retransfused blood group increased to about 110% relative to immediately before the blood removal by retransfusing blood. The blood pressure of each of the cyc group and piv group increased to about 85% relative to immediately before the blood removal by administering the test substance.

Figure 5:
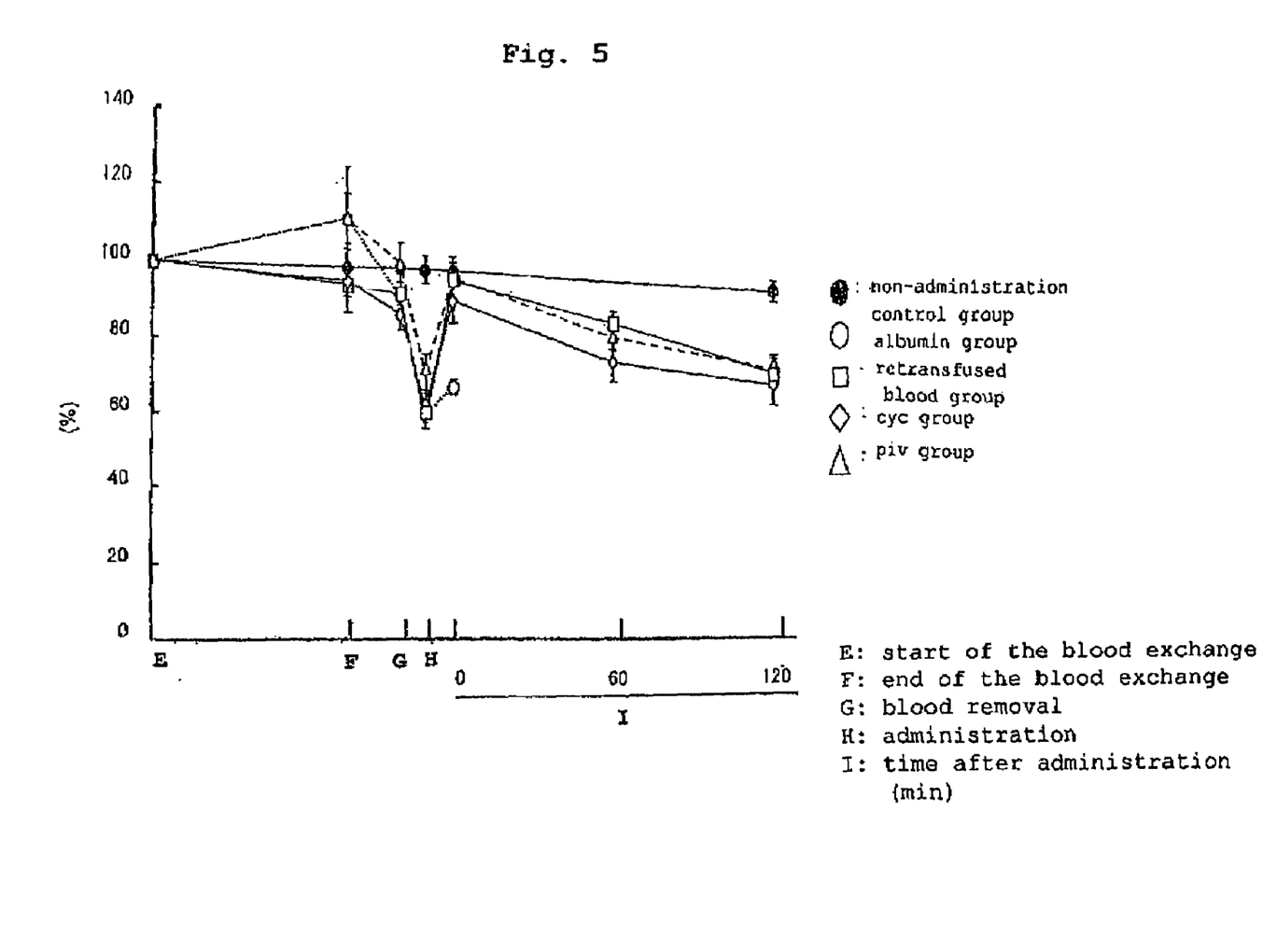
FIG. 5 A graph showing the improving effect of the present invention on decrease in oxygen partial pressure in venous blood.

FIG. 5 shows the result of the measurement of venous blood oxygen partial pressure. The venous blood oxygen partial pressure was measured for each of the albumin group, the retransfused blood group, the cyc group, and the piv group. The venous blood oxygen partial pressure decreased to about 90% relative to the initial level by exchanging 70% of blood. In addition, the venous blood oxygen pressure decreased to about 60% by removing 30% of blood. After that, the oxygen partial pressure of the albumin group did not increase even when albumin was administered, while the oxygen partial pressure of the retransfused blood group, the cyc group, or the piv group increased to about 110% relative to immediately before the blood removal by administering the test substance.

Effect of the Invention

As described above, the artificial blood of the present invention has both the oxygen carrying ability and colloid osmotic pressure (the plasma expanding effect), and is particularly effective for survival of a massive bleeding patient or the like.

Moreover, the artificial blood of the present invention can avoid hemolysis toxicity or the like because it is prepared by adjusting the crystalloid osmotic pressure, the electrolyte balance, and the pH value within biologically acceptable ranges.

In the present invention, a pharmaceutical composition having oxygen carrying efficiency as high as, or higher than, that of an erythrocyte can he prepared by using the oxygen carrier that is composed of a liposome-encapsulated hemoglobin or a conjugate of a metal complex having a porphyrin structure and albumin.

In addition, use of a liposome that contains a conjugate of a non-phospholipid lipid and a polyalkylene glycol can fix a water-soluble polymer stably on a liposome surface by intermolecular interaction and can bear the water-soluble polymer without detraction of the function thereof.

Moreover, use of recombinant albumin or hemoglobin can prepare a safe pharmaceutical composition that has no possibility of an infectious disease derived from a living body.

What is claimed is:

1. A pharmaceutical composition characterized by comprising a liposome-encapsulated hemoglobin capable of adsorbing and desorbing oxygen reversibly in a living body and albumin located on the liposome-encapsulated hemoglobin in a concentration to provide a colloid osmotic pressure of about 1 to 50 mmHg,
   wherein the liposome contains a conjugate of a lipid and a polyalkylene glycol and
   further wherein the composition is a liquid having said colloid osmotic pressure of about 1 to 50 mmHg, a crystalloid osmotic pressure of about 50 to 500 mOsm, P50 of about 1 to 50 Torr, and a pH of about 5.6 to 8.0.

2. The pharmaceutical composition according to claim 1, wherein the liposome contains a conjugate of a non-phospholipid lipid and a polyalkylene glycol.

3. The pharmaceutical composition according to claim 1, wherein the hemoglobin is a recombinant hemoglobin.

4. A blood infusion comprising the pharmaceutical composition according to claim 1.

5. An organ storage perfusion solution, an extra corporeal circulation solution, or a cell culture solution comprising the pharmaceutical composition according to claim 1.

* * * * *